US00PP34039P2

(12) United States Plant Patent
Kievit et al.

(10) Patent No.: US PP34,039 P2
(45) Date of Patent: Mar. 15, 2022

(54) ***HEUCHERA* PLANT NAMED 'BIG TOP CARAMEL APPLE'**

(50) Latin Name: *Heuchera x hybrida*
Varietal Denomination: Big Top Caramel Apple

(71) Applicant: Ball Horticultural Company, West Chicago, IL (US)

(72) Inventors: Christa Kievit, Hem (NL); Karl F. Batschke, Geneva, IL (US)

(73) Assignee: Ball Horticultural Company, West Chicago, IL (US)

( * ) Notice: Subject to any disclaimer, the term of this patent is extended or adjusted under 35 U.S.C. 154(b) by 0 days.

(21) Appl. No.: 17/460,258

(22) Filed: Aug. 29, 2021

(51) Int. Cl.
*A01H 5/02* (2018.01)
*A01H 6/80* (2018.01)

(52) U.S. Cl.
USPC ..... Plt./440

(58) Field of Classification Search
USPC ..... Plt./440
CPC ... A01H 5/02; A01H 5/12; A01H 5/00; A01H 6/80; A01H 1/107; A01H 1/121
See application file for complete search history.

*Primary Examiner* — June Hwu
(74) *Attorney, Agent, or Firm* — Audrey Charles

(57) ABSTRACT

A new and distinct cultivar of *Heuchera* plant named 'Big Top Caramel Apple', characterized by its medium greyed-red and medium green-colored foliage, medium yellow-green and white-colored flowers, and vigorous, mounded growth habit, is disclosed.

2 Drawing Sheets

Latin name of genus and species of plant claimed: *Heuchera* x *hybrida.*
Variety denomination: 'Big Top Caramel Apple'.

BACKGROUND OF THE INVENTION

The present invention relates to a new and distinct cultivar of *Heuchera* plant botanically known as *Heuchera* x *hybrida* and hereinafter referred to by the cultivar name 'Big Top Caramel Apple'.

The new cultivar originated in a controlled breeding program in Hem, The Netherlands during the summer of 2016. The objective of the breeding program was the development of *Heuchera* cultivars with unique foliage coloration and a vigorous, mounded growth habit.

The new *Heuchera* cultivar is the result of open-pollination. The female (seed) parent of the new cultivar is 'Carnival Watermelon', U.S. Plant Pat. No. 24,803, characterized by its immature foliage color of greyed burgundy-red with a slight silvery overlay and prominent reddish to reddish-brown venation, mature foliage color of greyed-green and prominent green venation, and moderately vigorous and mounded growth habit. The male (pollen) parent of the new cultivar is unknown. The new cultivar was selected as a single flowering plant within the progeny of the above stated open-pollination during July 2017 in a controlled environment in Hem, The Netherlands.

Asexual reproduction of the new cultivar by in vitro propagation since July 2017 in Tenjo, Colombia and Bremen, Germany has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Big Top Caramel Apple' as a new and distinct cultivar of *Heuchera* plant:

1. Medium greyed-red and medium green-colored foliage;
2. Medium yellow-green and white-colored flowers; and
3. Vigorous, mounded growth habit.

Plants of the new cultivar differ from plants of the female parent primarily in having foliage with less prominent venation and no silvery overlay on the upper surface, and increased growth vigor.

Of the many commercially available *Heuchera* cultivars, the most similar in comparison to the new cultivar is 'Carnival Candy Apple', not patented. However, in comparison, plants of the new cultivar differ from plants of 'Carnival Candy Apple' in at least the following characteristics:

1. Plants of the new cultivar have a foliage color that is greener than plants of 'Carnival Candy Apple';
2. Plants of the new cultivar have less prominent venation than plants of 'Carnival Candy Apple'; and
3. Plants of the new cultivar have greater growth vigor than plants of 'Carnival Candy Apple'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Big Top Caramel Apple'. The plants were approximately nine-months old. The plants were grown for approximately 15 weeks in 1.7-gallon containers in an outdoor shade nursery in West Chicago, Ill.

DETAILED BOTANICAL DESCRIPTION

Figure 1:
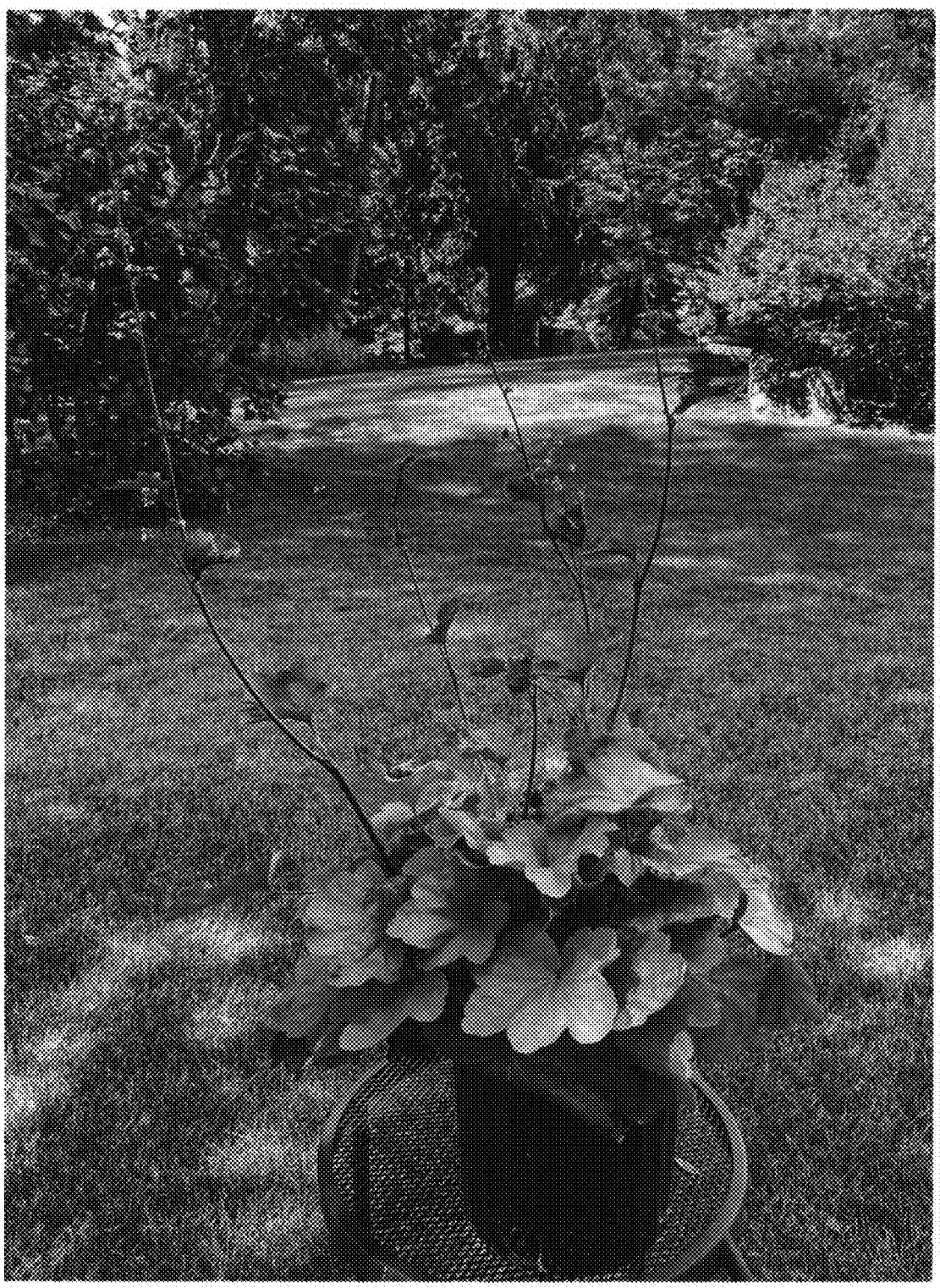
FIG. 1 illustrates a side view of the overall growth habit of 'Big Top Caramel Apple'.
Figure 2:
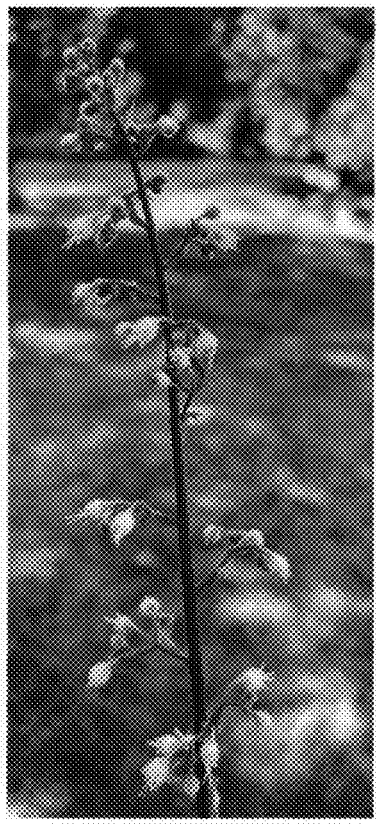
FIG. 2 illustrates a close-up view of an individual inflorescence of 'Big Top Caramel Apple'.
Figure 3:
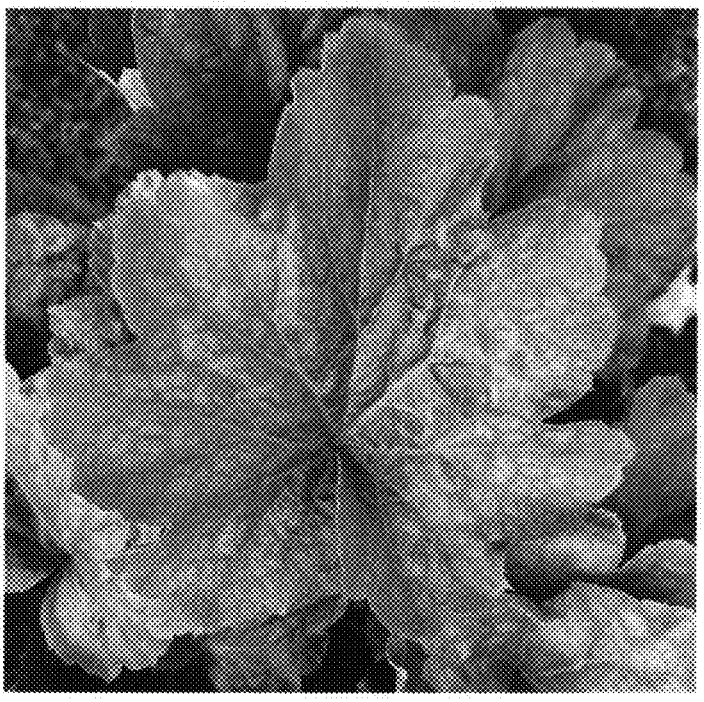
FIG. 3 illustrates a close-up view of an individual leaf of 'Big Top Caramel Apple'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2015 edition, except where general color terms of ordinary significance are used. The color values were determined in August 2021 under natural light conditions in Naperville, Ill.

The following descriptions and measurements describe approximately nine-month-old plants produced from in vitro plantlets and grown under conditions comparable to those used in commercial practice. The plants were grown in 1.7-gallon containers for approximately 15 weeks in an outdoor shade nursery in West Chicago, Ill. Prior to transplant plants were grown in liners in a poly-covered greenhouse in West Chicago, Ill. Greenhouse temperatures ranged from an average high of 79.5° F. (26.4° C.) to an average low of 68.5° F. (20.3° C.), and supplemental lighting was provided daily for five hours during short days. Measurements and numerical values represent averages of typical plants.

Botanical classification: *Heuchera* x *hybrida* 'Big Top Caramel Apple'.

Parentage:

*Female parent*.—'Carnival Watermelon', U.S. Plant Pat. No. 24,803.

*Male parent*.—Unknown.

Propagation:

*Type*.—In vitro propagation is preferred, divisions are possible.

*Time to initiate roots in vitro*.—Approximately 10 days at 20° C.

*Time to produce a rooted plantlet in summer*.—Approximately 42 days.

*Root description*.—Fine, fibrous.

*Rooting habit*.—Freely branching.

Plant description:

*Commercial crop time*.—Approximately 6 to 8 weeks from a rooted tissue culture plantlet to finish in a 10 cm container.

*Growth habit and general appearance*.—Clump-forming herbaceous perennial, mounded foliage.

*Growth rate*.—Vigorous.

*Hardiness*.—USDA Zone 4a (−30° F. to −25° F./−34.4° C. to −31.7° C.).

*Size*.—Height from soil level to top of plant plane: Approximately 80.0 cm. Height from soil level to top of foliage: Approximately 22.0 cm. Width: Approximately 53.0 cm.

*Branching habit*.—No branching, basal rosettes of leaves on petioles. Number of rosettes per plant: Approximately 7.

Foliage description:

*General description*.—Moderately durable to environmental stresses. Quantity of leaves per rosette: Approximately 12. Fragrance: None. Form: Simple. Arrangement: Alternate to whorled. Density: Dense.

*Leaves*.—Aspect: Blade is nearly perpendicular to petiole. Shape: Orbicular. Margin: Crenate with few and shallow indentations, moderately lobed, slightly wavy, ciliate. Apex: Minutely apiculate. Base: Cordate, typically slightly overlapping. Venation pattern: Palmate. Length of mature leaf: Approximately 14.0 cm. Width of mature leaf: Approximately 14.5 cm. Texture of upper surface: Dull, very weak rugosity, sparsely pubescent with short hairs. Texture of lower surface: Slightly glossy, sparsely pubescent with short hairs on venation. Color of upper surface of young foliage: Closest to 146A to 146B with a heavy overlay of closest to 178A, venation of closest to 177C. Color of lower surface of young foliage: Closest to 191C with a moderate overlay of N186D, venation of closest to 177D. Color of upper surface of mature foliage: 146A to 146C, margins occasionally tinted with 178A, venation of 146D faintly tinted with 187A; color not observed to change during fall season. Color of lower surface of mature foliage: Closest to 191C with an overlay of N186D and with base of main veins of closest to 147D; color not observed to change during fall season.

*Petiole*.—Length: Approximately 19.5 cm. Diameter: Approximately 3.0 mm. Texture: Sparsely pubescent. Color: 147D with an overlay of N186D, overlay is heavier on younger petioles.

*Stipules*.—Two leafy stipules located at the base of petioles. Apex: Acute. Length: Approximately 1.7 cm. Width: Approximately 5.0 mm. Color: Closest to N186D.

Flowering description:

*Flowering habit*.—'Big Top Caramel Apple' flowers once a year during late spring to midsummer under outdoor conditions.

*Lastingness of individual flower on the plant*.—Approximately 7 days.

Inflorescence description:

*General description*.—Type: Compound spike emerging from the base of the rosette with three to four cauline leaves. Density: Sparse. Fragrance: None. Length or height excluding the peduncle: Approximately 36.0 cm. Width: Approximately 6.0 cm. Quantity of inflorescences per plant: Approximately 4. Quantity of flowers per inflorescence: Approximately 70.

*Peduncle*.—Strength: Moderate. Aspect: Erect to approximately 40° angle from vertical. Length: Approximately 44.0 cm. Diameter at midpoint: Approximately 5.0 mm. Texture: Densely pubescent. Color: 146C with a heavy overlay of 187A.

Flower description:

*General description*.—Type: Single, campanulate, self-cleaning. Aspect: Drooping to slightly outward.

*Bud*.—Rate of opening: Generally takes 4 days for bud to progress from first color to fully open flower.

*Bud just before opening*.—Shape: Broadly obovate. Length: Approximately 3.0 mm. Diameter: Approximately 2.0 mm. Texture: Densely pubescent with a mixture of glandular and nonglandular hairs. Gland Color: 187A. Color: 158D with 146B.

*Corolla*.—Shape: Campanulate. Diameter: Approximately 4.0 mm. Depth: Approximately 5.0 mm.

*Petals*.—Quantity: 5. Arrangement: Single whorl. Shape: Narrowly elliptic. Appearance: Dull. Margin:

Entire. Apex: Acute. Base: Lower half fused into hypanthium. Length: Approximately 5.0 mm. Width: Less than 1.0 mm. Texture of upper and lower surfaces: Glabrous with glandular pubescent margins. Gland Color: Colorless, transparent. Color of upper and lower surfaces when first and fully open: NN155D with a faint overlay of N66C at apex.

*Calyx*.—Shape: Campanulate. Diameter: Approximately 4.0 mm. Depth: Approximately 4.0 mm.

*Sepals*.—Quantity per flower: 5. Shape: Elliptic. Appearance: Dull. Margin of free portion: Entire. Apex: Acute. Base: Lower half fused into hypanthium. Length: Approximately 4.0 mm. Width at rim of hypanthium: Approximately 1.5 mm. Texture of upper (inner) surface: Glabrous with upper half densely pubescent. Texture of lower (outer) surface: Densely pubescent with a mixture of glandular and nonglandular hairs. Gland Color: Mixture of 187A and colorless, transparent. Color of upper (inner) surface: NN155D with upper half of 146C. Color of lower (outer) surface: 155C with 146C at base and apex.

*Pedicel*.—Strength: Moderate. Aspect: The pedicel of the central flower of each spikelet is directly on top of the secondary pedicel, pedicels of secondary and tertiary flowers of each spikelet have an average 40° angle from vertical. Length: Approximately 5.0 mm. Diameter: Less than 1.0 mm. Texture: Densely pubescent with a mixture of glandular and nonglandular hairs. Gland color: 187A. Color: 146C with a heavy overlay of 187A.

*Reproductive organs*.—Androecium: Quantity: 5 per flower. Anther shape: Bilobed, ovoid. Anther length: Approximately 1.0 mm. Anther color: 34B. Filament length: Approximately 4.0 mm. Filament color: NN155D, opaque. Pollen amount: Not observed. Gynoecium: Pistil quantity: 2 per flower. Pistil length: Approximately 7.0 mm. Stigma shape: Pointed. Stigma color: NN155D. Style length: Approximately 3.0 mm. Style color: NN155D, opaque. Ovary color: 146D.

Seed and fruit production: Neither seed nor fruit production has been observed.

Disease and pest resistance: Resistance to pathogens and pests common to *Heuchera* has not been observed.

What is claimed is:

1. A new and distinct cultivar of *Heuchera* plant named 'Big Top Caramel Apple', substantially as herein illustrated and described.

* * * * *